United States Patent [19]

Pokhis

[11] Patent Number: 4,844,078

[45] Date of Patent: Jul. 4, 1989

[54] DEVICE FOR AND METHOD OF DETERMINATION EYE PRESSURE

[76] Inventor: Naum Pokhis, 1850 N. Whitley Ave., Hollywood, Calif. 90088

[21] Appl. No.: 851,926

[22] Filed: Apr. 14, 1986

[51] Int. Cl.$^4$ .............................................. A61B 6/13
[52] U.S. Cl. .................................... 128/645; 335/128; 652/81
[58] Field of Search ................... 128/645, 652; 73/79, 73/81, 85

[56] References Cited

U.S. PATENT DOCUMENTS

| 3,965,727 | 6/1979 | Argabrite | 73/81 |
| 4,523,597 | 6/1985 | Sawa et al. | 128/652 |

FOREIGN PATENT DOCUMENTS

| 5046672 | 6/1974 | Australia | 128/652 |
| 61777 | 10/1982 | European Pat. Off. | 128/652 |
| 395067 | 8/1970 | U.S.S.R. | 128/652 |

OTHER PUBLICATIONS

Perkins, "A Simple Applantion Toneneker", Transact., Opthalmologic Soc. of the U.K., vol. 73, pp. 26–66, 1953.

Mackay et al., "Fast Automatic Ocular Pressure Measurement...", IRE Transac. on Med. Elect., pp. 61–67, (1960).

*Primary Examiner*—Edward M. Coven
*Attorney, Agent, or Firm*—Ilya Zborovsky

[57] ABSTRACT

A loading element is brought into contact with an eyelid of a closed eye under load so that the eyelid produces on a surface of the loading element an imprint with a size which is inversely proportional to eye pressure. Two loading elements formed as cylinders can be provided for producing simultaneously imprints of the eyelids of both eyes, and they can be mounted on a spectacles frame.

2 Claims, 1 Drawing Sheet

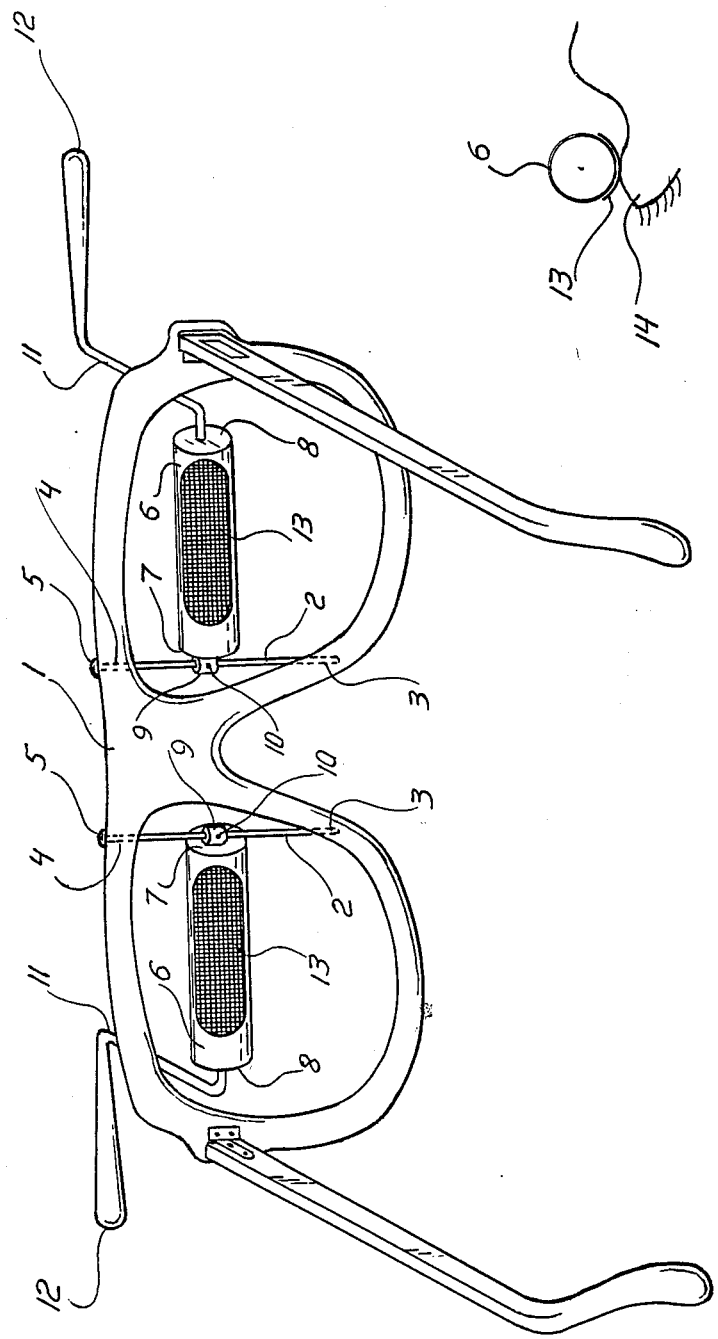

DEVICE FOR AND METHOD OF DETERMINATION EYE PRESSURE

BACKGROUND OF THE INVENTION

The present invention relates to a device for and a method of determination an eye pressure.

There are known several devices for determination of eye pressure. These devices have a complicated construction, they are too expensive to be used by common customers, they are used only by professionals with the use of anaesthesic drugs. As a result of this, people must frequently visit a physician, since otherwise they can miss a proper time for taking required measures to maintain good eyes and general health.

SUMMARY OF THE INVENTION

Accordingly, it is an object of the present invention to provide a device for and a method of determination of eye pressure, which avoids the disadvantages of the prior art.

More particularly, it is an object of the present invention to provide a device for and a method of determination of eye pressure, with the aid of which a person can at least approximately determine his or her eye pressure himself or herself without visiting a physician and in a simple and inexpensive manner.

In keeping with these objects and with others which will become apparent hereinafter, one feature of the present invention resides, briefly stated, in a method and a device, in accordance with which a loading element is applied onto an outer surface of an eyelid, the eyelid and the eye are deformed under the action of the loading element inversely proportionally to the eye pressure, and when a marking material is applied on the outer surface of the eyelid or the loading element an imprint is formed on a surface of the loading element so that the size of the imprint is a measure of the eye pressure.

The novel features of the present invention are set forth in particular in the appended claims. The invention itself, however, both as to its construction and method of operation, will be best understood from the following description of a preferred embodiment which is accompanied by the following drawings.

BRIEF DESCRIPTION OF THE DRAWINGS

FIG. 1 is a perspective view of an inventive device for determination of eye pressure; and FIG. 2 is a vertical cross section of contacting eye lid and the device.

DESCRIPTION OF A PREFERRED EMBODIMENT

A device for determination of eye pressure can be used in association with a spectacles frame identified with reference numeral 1. Two axles 2 are arranged at both sides of the axis of symmetry of the frame. The lower ends of the axles 2 abut against bottoms of blind holes 3 provided in the frame 1. The upper ends of the axles 2 are passed through openings 4 and are closed by plugs 5.

The device further includes two hollow cylinders 6. One closed end of each of the cylinders is provided with a bush 9 which is attached to an end cover 7 of the closed end and is fitted on the respective axle 2. The bushes 9 are fixed at the level of person's pupils by means of set screws 10. Another closed end of each cylinder is provided with a cover 8. Shaped handles 11 with thickened parts 12 are connected with the covers 8. Dark smooth films 13 provided with graduation marks are attached to the outer surface of the cylinders 6 and more particularly to the part of the surface, which faces toward the eyes.

The device operates in the following manner: The outer surface of eyelids is provided with a thin layer of oil. The eyelid is identified in FIG. 2 with reference numeral 14. A thin layer of powder, for example, talcum is applied into the graduated films 13 of the cylinders 6. A person lies onto a horizontal support, for example, a bed, a table etc. With one hand, the person turns the cylinders 6 rearwardly in FIG. 1 around the axles 2 so that the handles 12 approach one another and the person holds them together with one hand. Then the person puts the frame 1 onto the nose. He closes his eyes, lifts eyebrows as high as possible, and directs the pupils straight upwardly and holds them immovably. Then the person turns the handles 12 one after the other so that the graduated film 13 of the cylinders 6 slightly touches the highest point of the eyelids, and then smoothly and simultaneously releases the handles. After approximately 3 sec. the handles 12 are carefully lifted with the axles 2, the handles are brought together again and held with one hand, and the frame 1 is removed from the nose with the other hand. An imprint of an oval shape is formed on the films 13. The higher is the eye pressure, the smaller is the deformation of the eyelids and the eyes and the smaller is the imprint. The horizontal long axis of the oval imprint is measured by the graduations on the films, so that no additional measuring instrument is needed. It is desirable to make several such measurements for each eye and to determine an average length of the oval imprint.

Knowing his or her eye pressure measured by a physician and comparing it with the data received in the inventive device, namely the size of the long axis of oval, a person determines, just once, the relationship between the real eye pressure and the above size. Then, after determination of this relationship, he or she will be able to determine his or her eye pressure based solely on the size of the imprint, namely on the length of the long axis of oval.

It is to be understood that the device can be somewhat different. The cyliders can be mounted not on a frame, but on another carrier. There can be only one cylinder which successively is used for both eyes. Finally, the element which gets the imprint must not be necessarily cylindrical, it may have another shape.

The invention is not limited to the details shown since various modifications and structural changes are possible without departing in any way from the spirit of the invention.

What is desired to be protected by Letters Patent is set forth in the appended claims.

I claim:

1. A device for determination of eye pressure, comprising
    a spectacle frame having holes;
    two cylinders having cylindrical outer surfaces and moveable between a distal position in which they are withdrawn from said holes of said frame and a proximal position in which they are arranged substantially in the region of said holes and their cylindrical surfaces are brought into contact with eyelids of person's eyes;

an imprintable material applied on said cylindrical surfaces of said loading elements; and a graduated surface provided on each of said cylinders so that in said proximal position the eyelids produce imprints on said graduated surface of said cylinders and the size of said imprints can be determined by graduations of said graduated surfaces, which size is inversely proportional to eye pressure.

2. A method of determination of eye pressure, comprising the steps of providing a loading element formed as a cylinder having a cylindrical surface;

applying onto said cylindrical surface an imprintable material;

bringing the surface of the loading element coated by the imprintable material into contact with an outer surface of an eyelid of a closed eye so that the cylindrical surface of said cylinder of the loading element is in contact with the spherical outer surface of the eyelid imparted by the eye, so that the eyelid produces on said surface of said cylinder of said loading element an imprint; and determining a size of the imprint on said cylinder of said loading element, which size is inversely proportional to eye pressure in the eye.

* * * * *